US009494511B2

(12) United States Patent
Wilkins (10) Patent No.: US 9,494,511 B2
(45) Date of Patent: Nov. 15, 2016

(54) SYSTEM AND APPARATUS FOR MEASUREMENT AND MAPPING OF POLLUTANTS (75) Inventor: Steven Wilkins, Bristol Avon (GB)

(73) Assignee: DUVAS TECHNOLOGIES LIMITED, London (GB)

( * ) Notice: Subject to any disclaimer, the term of this patent is extended or adjusted under 35 U.S.C. 154(b) by 725 days.

(21) Appl. No.: 13/139,884

(22) PCT Filed: Dec. 21, 2009

(86) PCT No.: PCT/EP2009/067694
§ 371 (c)(1),
(2), (4) Date: Jun. 15, 2011

(87) PCT Pub. No.: WO2010/070147
PCT Pub. Date: Jun. 24, 2010

(65) Prior Publication Data
US 2011/0251800 A1 Oct. 13, 2011

(30) Foreign Application Priority Data
Dec. 19, 2008 (EP) .................... 08172470

(51) Int. Cl.
G06F 19/00 (2011.01)
G01N 21/33 (2006.01)
(Continued)

(52) U.S. Cl.
CPC ............... *G01N 21/33* (2013.01); *G01J 3/02* (2013.01); *G01J 3/0264* (2013.01);
(Continued)

(58) Field of Classification Search
USPC .............. 702/24; 340/905, 601, 995.12, 435, 340/995.14; 701/301, 117, 45, 469
See application file for complete search history.

(56) References Cited

U.S. PATENT DOCUMENTS 6,246,960 B1 * 6/2001 Lin ................... G01C 21/165
701/472
6,405,132 B1 * 6/2002 Breed ................... B60N 2/002
701/117

(Continued)

FOREIGN PATENT DOCUMENTS

EP 1113268 7/2001
EP 1942342 7/2008

OTHER PUBLICATIONS

Tai, Hideo, "Urban Gas Monitoring System Using Optical Sensors," *Proceedings of the SPIE*, SPIE, Bellingham, VA, USA, vol. No. 3746, p. Nos. 332-336, Jan. 1, 1999.
(Continued)

Primary Examiner — Manuel L Barbee
(74) Attorney, Agent, or Firm — Christopher J. McKenna; Foley & Lardner LLP (57) ABSTRACT Apparatus and systems, preferably using UV spectroscopy, for the dynamic and continuous detection and quantification of a range of chemicals, particularly pollutants, in the environment, and to the production of a real-time display or map to display chemical levels in the environment are provided. By providing data packets which combine details of pollutants in the atmosphere with very accurate position and temporal information, and real-time map of pollution is provided.

17 Claims, 8 Drawing Sheets (51) Int. Cl.
  *G01J 3/02* (2006.01)
  *G01N 21/03* (2006.01)
  *G01N 33/00* (2006.01)
  *G01N 21/17* (2006.01)
  *G01S 19/14* (2010.01)
  *G01S 19/49* (2010.01)

(52) U.S. Cl.
  CPC ......... *G01N 21/031* (2013.01); *G01N 33/0004* (2013.01); *G01N 2021/1795* (2013.01); *G01N 2201/0216* (2013.01); *G01N 2201/0221* (2013.01); *G01S 19/14* (2013.01); *G01S 19/49* (2013.01)

(56) References Cited

U.S. PATENT DOCUMENTS

| | | | |
|---|---|---|---|
| 6,415,646 B1 | 7/2002 | Kessel et al. | |
| 6,750,467 B2 | 6/2004 | Tulip | |
| 6,822,742 B1 | 11/2004 | Kalayeh et al. | |
| 7,288,770 B2 | 10/2007 | Gamiles et al. | |
| 2004/0189976 A1 | 9/2004 | Burns et al. | |
| 2006/0237657 A1 | 10/2006 | Gamiles et al. | |
| 2008/0024323 A1* | 1/2008 | Kadaba | G01N 33/0075 340/905 |
| 2009/0203352 A1* | 8/2009 | Fordon | H04M 15/00 455/406 |

OTHER PUBLICATIONS

International Search Report issued in International Application No. PCT/EP2009/067694, mailed on Apr. 26, 2010.
European Search Report on EP Application No. 08172470 dated May 19, 2009.
International Preliminary Report on Patentability on PCT/EP2009/067694 mailed on Jun. 30, 2011.

\* cited by examiner

The prediction-correction nature of the Kalman filter

FIGURE 6

How a Kalman filter can be applied to a combination of GPS and IMU/INS data

FIGURE 7

The IMU/INS strapdown method

FIGURE 8

A loosely coupled GPS-IMU/INS system

FIGURE 9

A tightly coupled GPS-IMU/INS system

FIGURE 10

An ultra-tightly coupled GPS-IMU/INS system

SYSTEM AND APPARATUS FOR MEASUREMENT AND MAPPING OF POLLUTANTS

CROSS-REFERENCE TO RELATED APPLICATIONS

This application is a National Phase Application of PCT International Application No. PCT/EP2009/067694, International Filing Date Dec. 21, 2009, claiming priority of European Patent Application No. 08172470.0, filed Dec. 19, 2008, each of which being hereby incorporated by reference in its entirety.

FIELD OF INVENTION

The present invention relates to systems and apparatus, preferably using differential and/or conventional ultraviolet (UV) spectroscopy, for the dynamic and continuous detection and quantification of a range of gaseous or airborne chemicals, particularly pollutants, in the environment, and to the production of a real-time display or map to display chemical levels in the environment.

BACKGROUND OF INVENTION

Urban air pollution is widely recognised as being one of the greatest environmental concerns to those living or working in urban areas. The need for monitoring and obtaining highly accurate measurements of the pollution is growing constantly due to the demands of governmental institutions, environmental consciousness, and new legislation. This high accuracy of measurement is required to produce representative high resolution maps or accurate and precise positional data of pollution levels or other environmental factors in urban areas e.g. during rush hours, which can be studied to better control the urban environment, such as traffic flow management.

Unfortunately, conventional measurement systems do not provide the highly accurate detection of gases in air as required, nor do they provide a real-time map. These systems normally collect data over timescales of the order of minutes. The pollution levels are often retrieved from samples removed from the point of measurement, making correlations with pollutant sources difficult.

Other systems use fixed location stations and are usually sparsely distributed, e.g. by the roadside, that provide information data about the pollution in situ. However, it is not possible to monitor an extensive area with fixed stations and only a limited number of areas can be monitored by such as system. Furthermore, such fixed systems cannot provide a widely based real-time map. Conventional systems are also limited to being fixed near to the roadside rather than able to measure concentration values closer to the centre of road junctions or along the road itself. Conventional systems are usually set up to measure only one pollutant or other environmental factor. Furthermore, in some cases the pollutant is not measured directly, but is an extrapolated value.

Accordingly, mobile devices have been introduced to monitor the pollution levels in the atmosphere. Mobile devices here are being defined as devices capable of taking continuous measurements whilst being transported between geographic locations, e.g. those which can be mounted onto road vehicles, or carried by hand, These mobile devices are flexible and have an extensive spatial coverage. The disadvantage associated with known monitoring systems using such mobile devices is the lack of accuracy of the measurements, and limited response time, when monitoring pollution levels.

U.S. Pat. No. 6,750,467 discloses a mobile gas detector comprising a laser transmitter and signal analyzer carried on a vehicle and a laser absorption cell carried on the exterior of the vehicle.

U.S. Pat. No. 7,288,770 discloses a portable air monitoring system using UV spectroscopy capable of detecting chemicals in the open atmosphere or in a sample of air which is introduced into a chamber. The system enhances its sensitivity and accuracy by collecting a full spectrum of data points and by using multiple mirrors to increase the beam path in a closed-path length. The accuracy of these methods is good but not sufficient to fulfil the requirements that are present today, such as forming representative maps of pollution levels.

U.S. Pat. No. 6,415,646 relates to a method for the measurement of gas concentrations with a measuring head which is provided with a satellite-supported global positioning device. The position of the measuring head is determined at predetermined time intervals and positional data compared. A measured value of gas concentration corresponding to positional information can be stored in a data memory.

EP 1,942,342 describes a detection system employing trained animals. Biometric data can be collected from the animal to determine the change in body position of the animal. Thus, by analysing the body position of the animal, it can be determined whether the animal has detected a target odour. The positional information of the animal can be determined by a GPS system supplemented with an inertial navigation system. There is no means described for mapping the environmental data.

US 2006/0237657 describes real time UV spectroscopy for the quantification of gaseous toxins using open-path or closed multipass white cells. The system can be used in a portable system for UV spectroscopy capable of the detection and quantification of chemicals from either open air environments or by insertion of a sample using a sample chamber. The system can, for example, be mounted on the rooftop of a vehicle.

US 2008/0024323 describes a mobile system for monitoring travel conditions, in particular air quality. An air monitoring device can be mounted on a vehicle to collect air quality data combined with the data relating to the physical location of the vehicle. A central computer can be configured to analyse the air quality data and disseminate the information in near real time such that recipients can alter their behaviour based in part on the results.

Hideo Tai in Proceedings of the SPIE, Vol. 3746, pages 332-336 describes a methane monitoring system installed n a vehicle with a positioning system and a mobile GIS that enables real time recordal of gas leakage from buried pipelines.

EP 1,113,268 describes a method and apparatus for air quality monitoring in a predetermined geographical area wherein GPA data can be used to plot the position of the vehicle collecting the air quality samples.

In the prior art, measurements are made as the vehicle moves along, but cannot be translated into any sort of real-time map due to the lack of accurate position data required in an urban or built up environment, particularly where GPS information can be difficult to obtain.

The position calculated by a GPS receiver requires the current time, position of the satellite and the measured delay of the received signal. The position accuracy is primarily dependent on the satellite position and signal delay. To measure the delay, the receiver compares the bit sequence received from the satellite with an internally generated version. By comparing the rising and trailing edges of the bit transitions, modern electronics can measure signal offset to within about one percent of a bit time, or approximately 10 nanoseconds for the C/A code. Since GPS signals propagate at the speed of light, this represents a theoretical error of about 3 meters. Position accuracy can be improved by using the higher-chip rate signal, however, typical electronics errors are one of several accuracy-degrading effects When taken together, autonomous civilian GPS horizontal position fixes are typically accurate to about 15 meters (50 ft).

Additionally GPS signals can also be often affected by multipath issues, where the radio signals reflect off surrounding terrain; buildings, canyon walls, hard ground, etc. These delayed signals can cause inaccuracy. A variety of techniques, most notably narrow correlator spacing, have been developed to reduce multipath errors, but cannot be mitigated completely and remain a significant problem. In these environments such as an urban environment or structure-rich environment, the GPS positioning data is further corrupted very significantly or even blocked completely. This is caused by multi-pathing of GPS signals reflecting of large structures, sudden variations in positions occurring from different satellites coming into view, or limitations imposed from low-cost electronics or reception.

In the instance of multi-pathing or blockage, we can consider that the accuracy of GPS may be limited over long time periods, whereas for short-term or real-time measurements the precision of GPS determined coordinates may not be sufficient.

A speed profile obtained from the GPS data will be obtained as discrete values because the measurements of speed were performed at 1 second intervals (1 Hz). Such time series are overlaid with high frequency noise signals showing spikes in the profile. In order to remove this noise signal, a smoothing filter can be applied. However, although some smoothing filters of position may be possible, short-term accuracy may not be significantly improved.

GPS can provide height information, and additionally, GPS height information can be improved through the inclusion of additional GPS receivers mounted some distance apart. Height information is especially relevant to low level airborne sensors, such as those mounted on UAVs.

In scrutinising environmental factors, it is recognised that these factors typically vary over extremely short geographical distances, particularly in urban environments. Therefore it is necessary to collect very localised data as to environmental factors. Utilising only GPS positioning data is not sufficient to provide accurate and precise geographical positioning particularly over short timescales, but the problem is even more severe in an urban or other structure-rich environment.

SUMMARY OF INVENTION

According to an object of the present invention, there is provided a system for mapping environmental factors in the atmosphere having one or a plurality of mobile detection apparatuses, wherein each detection apparatus comprises;
  a sensor for detecting environmental factors in the atmosphere which provides data relating to an atmospheric sample;
  a navigation system for tracking the geographic position of the sensor and time the sample is taken;
  a processing unit capable of processing data;
  the processing unit being coupled to said sensor and navigation system in order to provide the geographic position and time of each sample;
said system further comprising a server including a database where data from each apparatus is stored and, optionally processed, characterised in that said navigation system comprises a first navigation means comprising a GPS system and a second navigation means comprising an independently functioning positioning system, wherein said first and second navigation means are data-coupled and wherein each mutually informs the other and provides accurate and continuously refined and corrected position data and optionally velocity data.

One embodiment of the invention provides position, direction and velocity data in such a way that the sensor or data relating to the environmental factors can be dynamically manipulated in order to provide optimized data.

Each detection apparatus can comprise a processing unit capable of processing data from a sensor for detecting gases in a closed optical path (i.e. one which does not extend beyond the confines of the device); a navigation system for tracking the position of the one or plurality of apparatuses wherein the processing unit is coupled to said sensor and navigation system; and preferably means for transmitting data back to a central location.

The invention also provides a method for the production of real-time locational information of environmental factors which comprises;
  taking an atmospheric sample and analysing the sample in a spectrometer;
  taking a geographical position of where the atmospheric sample was taken and coupling this geographic information with time information to provide a very accurate time and position of the sampling point;
  combining the position, time and analysis results into a packet of data and transmitting the packet of data to a server;
  analysing the information of the atmospheric sample to provide data of the level of environmental factors
  integrating the data of the environmental factors with real-time position data to provide real time location of environmental factors,
characterised in that geographical information is produced from a navigation system comprising a first navigation means comprising a GPS system and a second navigation means comprising an independently functioning positioning system, wherein said first and second navigation means are data-coupled and wherein each mutually informs the other and provides accurate and continuously refined and corrected position data and optionally velocity data.

The above system and methodology provides real-time simultaneous concentration measurements of atmospheric chemicals due to the navigation system used in each apparatus. The results are highly accurate measurements of pollution levels which can be used to form a map showing the distribution of pollution or other environmental factors. The data can preferably be layered onto a geographic map of an area to form a map of environmental factors (such as pollution levels) in relation to known points such as roads, houses, factories and so on. Different mixes of emissions detected simultaneously can also be used for source apportionment.

Moreover, such a system enables real-time and continuous monitoring of pollutant levels over short timescales, or localised geographical areas for the purposes of high resolution mapping or correlation of other data spatially or temporarily.

By real-time we mean a monitored system where as much information as possible is provided continuously with a short time delay. It will be understood that some measurements will be contemporaneous, whilst others will be historic, but the aim is that historic values should be updated as frequently as possible to provide as good a real-time information measurement as possible over the measured area. Fuzzy logic can be used to update the modelling of measurements as required, based on other exact and real-time readings.

In addition, the system for monitoring urban air pollution can be used for portable, mobile, and fixed apparatuses. Such systems could monitor an entire city if large enough numbers of robust systems could become available to local authorities or concerned parties.

In a preferred system, each apparatus is mobile. Such an apparatus can be mounted on cars, motorbikes or surface mass transportation vehicles allowing for large area coverage. The apparatus can also be designed to be portable.

In a preferred system, the first navigation means comprises one or more GPS receivers and the second navigation means comprises a positioning system other than GPS. Most preferably, the second navigation system comprises an IMU/INS system.

The accuracy of a measurement system may be defined as the degree of closeness of measurements of a quantity to its actual true value. The precision of a measurement system, also called reproducibility or repeatability, is the degree to which repeated measurements under unchanged conditions show the same results.

Preferably, there is provided a system, wherein each navigation system includes one or more GPS (Global Positioning System) receivers. As discussed although GPS offers high-resolution positioning information on or about surface level, it does not directly obtain information about vehicle orientation or speed. Commercial systems which are GPS-based such as SatNav systems rely on road-maps to locate the vehicle to the nearest road as a best-guess when positional data becomes unreliable. More preferably a navigation system comprises a GPS linked to an alternative navigation system such as a radio navigation system (RDF) or a dead reckoning system. Dead reckoning is the process of estimating present position by projecting course and speed from a known past position. A preferred type of dead reckoning navigation system is inertial navigation, whereby position is computed based on motion sensors. Thus, most preferably, the navigation system comprises a GPS linked to an IMU (Inertial Measurement Unit)/Inertial Navigation System (INS). Integration of GPS information with other sensor data such as IMU/INS enables a continuous and accurate estimate of position to be provided on a real time basis. In an urban environment, the GPS satellite may be hidden from the receiver due to high buildings or other local geographical features. By integrating a GPS receiver with an IMU/INS a much greater degree of navigational and positional accuracy can be obtained. Thus the use of a coupled GPS-IMU/INS provides accurate telemetry data allowing for the accurate assessment of the pollution levels over a wide area. This allows a greater monitoring coverage than existing fixed monitor sites.

The detection apparatus can be a spectrometer or interferometer detecting in the wavelength of ultraviolet, ultraviolet-visible light, infrared or a combination thereof. Preferably, the detection apparatus comprises an instantaneous ultraviolet gas analyzer. The ultraviolet (UV) spectrometer is able to collect high resolution data for analysis of a broad range of gases. The present invention detects in particular gases in the UV (wavelength range of 160-500 nm), visible (wavelength range of 500-800 nm), and IR (wavelength range of 800-15000 nm), The spectrometer is capable of detecting multiple gases at trace levels. Raw data can be collected in intensity vs. wavelength format. Signal strength is monitored and logged, and linked to navigation data.

Preferably, there is provided a system, wherein the sensor data is processed over a dynamically-variable sample period. The sample period can be adjusted automatically by the apparatus processor itself or remotely, based upon information from the IMU/INS.

According to another object of the present invention, there is provided a mobile device for mapping pollution levels comprising a processing unit capable of processing data from a sensor for detecting gases in a closed optical path and from a navigation system, wherein the processing unit is coupled to said sensor and navigation system. The navigation system preferably comprises an integrated GPS-IMU/INS system.

BRIEF DESCRIPTION OF THE FIGURES

The invention will be further described with reference to the accompanying figures, in which.

DETAILED DESCRIPTION

An embodiment of the present invention is a networked system having a plurality of integrated apparatuses comprising navigation means and gas sensors connected to each other via a server. The server includes a database where the output data is stored. Each apparatus comprises a computer with a processing unit capable of processing data from a sensor for detecting gases, preferably in a closed optical path, most preferably a optical ultraviolet multi-pass arrangement such as a White cell, Cavity Ring-Down, Integrating Sphere, or Herriott cell. Each apparatus can integrate this information with a navigation system to provide a packet of information which shows at any instant the various pollutant levels in relation to the geographic position of the gas sensor.

The sensor, which is as noted is preferably a UV spectrometer, detects, but is not limited to the detection of, nitrogen monoxide, nitrogen dioxide, sulphur dioxide, ozone, ammonia, hydrogen sulphide, benzene, toluene, (m-, o-, p-) xylene, isobutylene, nitrous acid, hydrogen fluoride, mercury, styrene, carbon disulphide, formaldehyde, acetaldehyde, phenol, (m-, o-, p-), cresol, chlorobenzene, dichlorobenzene, hydrochloric acid, hydrogen cyanide, hydrogen bromide, chlorine dioxide, chlorine, phosgene, ethylbenzene, acrylonitrile, 1,2,4-trimethylbenzene, 1,3,5-trimethylbenzene, and others.

Figure 1:
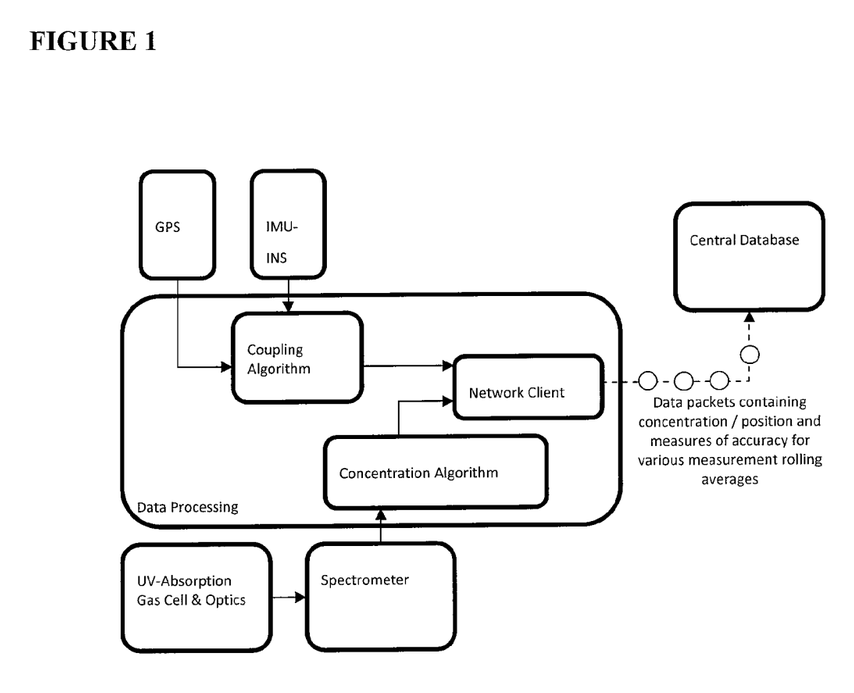
FIG. 1 shows a general data flow diagram of how the data is transmitted
Figure 2:
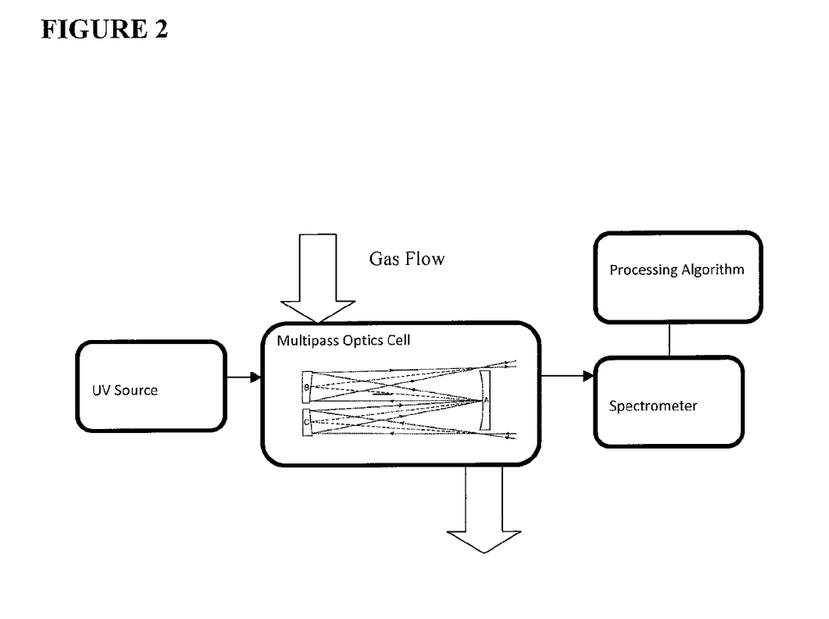
FIG. 2 shows a schematic diagram of the optics used in a UV spectrometer as preferred in the present invention

FIG. 2 shows a diagrammatic arrangement of the UV spectrometer, having a UV source which passes through a closed path optics cell. Gas passes through the optics chamber, and the resultant spectral image is received by a spectrometer. The information can then be processed to analyse the composition of the gas, e.g. constituent chemicals and the amount of these chemicals, by a processing algorithm.

In order to detect the gases, it is necessary to create a reference "library" of spectra for each gas, such that a gas' unique signature can be recognised and quantified. Any number of gases which absorb UV light can be added to the library in order to provide the basis for a wide range of pollutant detection. The general advantages of this approach are that such devices have extendable capabilities beyond an initially configured set of gases. Configurable devices able to tune to the specifics of an event is a desirable quality in the deployment of a permanent sensor network.

Figure 3:
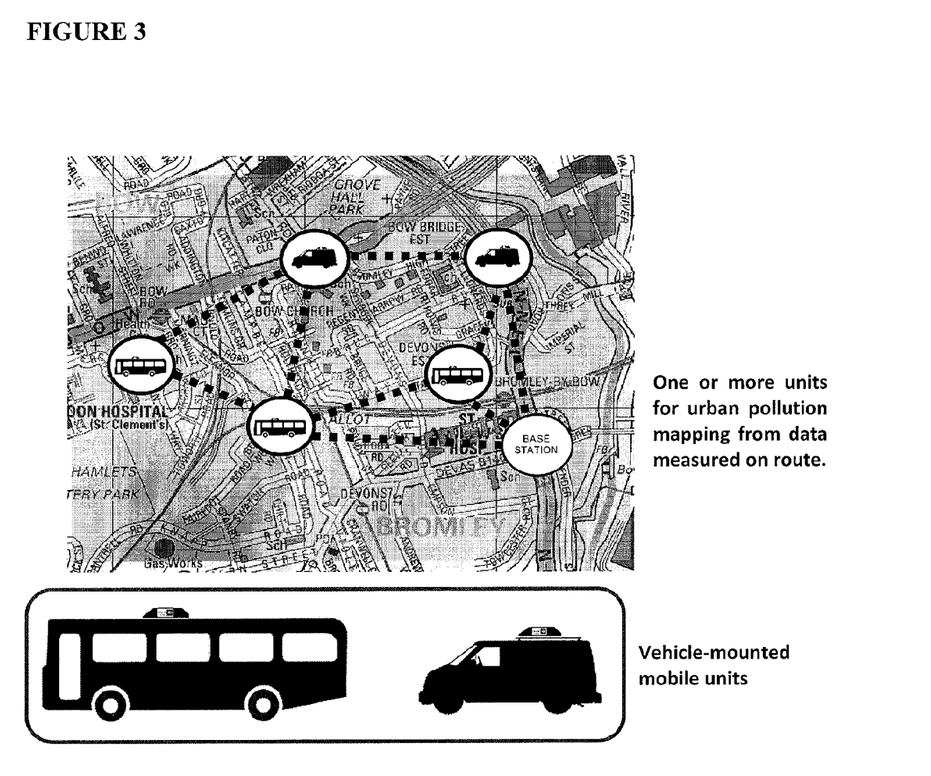
FIG. 3 shows a networked system in an urban environment.
Figure 4:
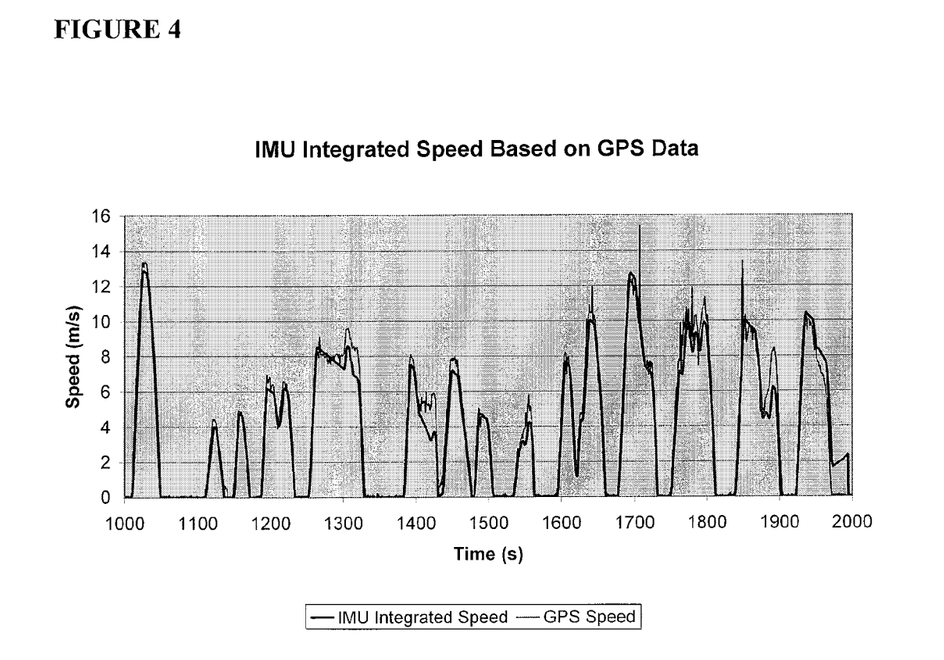
FIG. 4 shows an example comparison between GPS and IMU derived speed

The networking apparatuses may be placed in fixed locations around a specific area, but are preferably mobile and attached to a moving vehicle. FIG. 3 shows a representation of vehicle mounted units recording pollutant levels for map generation. Each vehicle has, mounted on the roof, a small UV spectroscopic gas analyser. Information on local pollution levels is sent back to a central server, which can then produce a visual map of the pollutant composition and levels. The individual measuring apparatuses are networked together, preferably by an ad hoc communication system, complementary to or instead of a fixed infrastructure system. This allows ease of data transfer, even if a fixed receiver is not easily available for data transmission. Data is easily transferrable in an urban environment over GSM/GPRS cell-phone networks. Most preferred is a multi-hop ad hoc network, whereby information can be stored in the apparatus, and then transmitted to a receiver on an as and when basis. Each apparatus could function as a joint transmitter and receiver, allowing for transmission of multiple data packets.

There is also provided a navigation system for tracking the position of gases detected by the UV spectrometer. In this case, the navigation system is preferably combined one or more Global Positioning System (GPS) receivers, and Inertial Measurement Unit system (IMU)/Inertial Navigation System (INS), which is connected to a computer or an embedded microprocessor unit.

Distributed sensor networks naturally lend themselves to ad-hoc wifi networks, but can also use infrastructure networks such as WiMax. These systems are able to use Bluetooth, GPRS, 3G or a combination of the above for mixed-mode data transfer. Accurate mapping generation is only possible through the hardware configuration and the advantage and benefit of the present invention is based on the generation of high quality data rather than focusing on the post processing of the acquired data.

In a preferred embodiment of the present invention, the data detected by the sensors is bundled and transferred over a suitable non-wired architecture, either directly, or routed via neighbouring nodes. Intermittent ad hoc WiFi is a preferred choice for such transfer. However, as explained above, the system robustness is improved with a mix of communication technologies. In the present invention, a map is to be understood as defining not only a geographic representation, but any system allowing for graphic and/or figurative representation of a measured phenomenon, including for example bar charts and numeric read outs, tied to a geographic location.

A central database on a server is then able to either directly make use of the data in a visual form by layering of information onto a geographic map, integration with SMS-based alerts to groups and individuals, coupling with dispersion modelling packages for increased accuracy, and so on. Dispersion models are normally pollution inventory based and not an accurate approximation of actual pollution levels but can be complemented with the data from the database for an accurate result.

If a pollution or emission event occurs which needs to be monitored, the sensor network with a plurality of sensors or apparatuses may have its behaviour altered centrally via the central logging server to be able to measure pollution events such as sudden gas plumes of a factory starting up, ships coming into harbour, TIC releases, CWA attacks, and so on.

As noted, one preferred aspect of the present invention is the integration of GPS and Inertial Measurement Unit (IMU)/Inertia Navigation System (INS) data. The GPS signal is used to correct or calibrate the information from an IMU/INS. IMU/INS systems comprise of a number of sensors to measure accelerations along a number of axes. Typically an IMU/INS system will consist of the measurement of a series of mutually orthogonal linear and rotational accelerations, but additional sensors (or IMU/INSs) may be used to supplement readings. The IMU/INS provides high frequency acceleration/rotation rate data, which is coupled loosely, tightly, or ultra-tightly coupled with GPS measurements. IMU/INS systems can provide accurate information for a short period of time, and as discussed.

GPS systems can have problems due to local geographical features blocking out satellite signals. Long-term, GPS gives a drift-free position that can be used to continuously reset the IMU/INS navigation system, or more preferably be coupled with the IMU/INS data (and measurement errors) by a mathematical algorithm such as a Kalman filter.

GPS data primarily is provided in latitude and longitude format. For some applications, like maps overlays or manual speed calculations, it is necessary to project the data and convert into meters. For medium and large scale sheet maps, or maps and projected coordinates held digitally to a high accuracy, it is essential that due regard is paid to the actual shape of the earth. Even though there are several projections available, one of the most used conversion from earth angles to meters is the Transverse Mercator Projection. This projection converts the latitude and longitude data into meter easting and meter northing.

A GPS system requires that four satellites are tracked in order to solve for three dimensional positions, where a fourth time uncertainty is also solved. With fewer than four satellites available, it is not possible to achieve stand-alone three dimensional GPS positioning. Varying number of satellites in urban, tree-covered, or tunnelled settings increase the uncertainty of positioning from GPS alone. As noted, the GPS system can be correlated with an IMU system to provide a much more accurate position plot.

Figure 7:
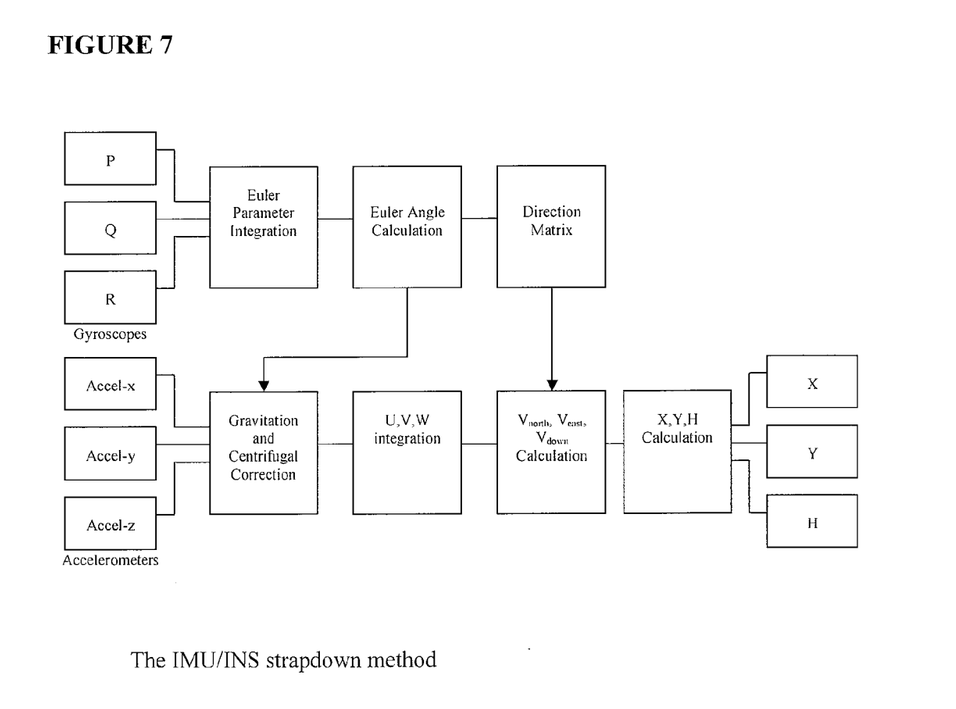
FIG. 7 shows the IMU/INS strapdown method.

Measurement data collected from the six linear and rotational acceleration sensors as part of the full IMU/INS system, are numerically compiled via a strapdown algorithm. The purpose of the algorithm is to take the acceleration data and to derive positional data. An IMU/INS strapdown method such as via a Kalman filter can be applied to combine each of the measurements from the sensors comprising the IMU/INS system. The data obtained from the IMU/INS is in the form of three orthogonal accelerations (x, y, and z) and one angular speed (yaw gyro rate) recording rotation in the z axis. Data provided from the IMU/INS is usually at a very high rate. FIG. 7 shows the IMU/INS strapdown Method. This data can be manipulated and integrated to generate speed profiles comparable with the ones obtained from the GPS solution. The speed profiles obtained from the IMU/INS validate the GPS speed profiles and "fill the gaps" for when the GPS looses reception. However, the integration algorithm from accelerations to speed is not straight forward and requires noise filtering and several corrections. The stage at which these data can be coupled is dependent on the level of sophistication of integration used, where physical and measured errors need to be considered. The main errors associated with any IMU unit are bias, scale factors and drift. Bias refers to the offset in the measurement provided by the inertial sensor caused by various imperfections within the sensor. Scale factor refers to the relationship between the output signal and the quantity which it is measuring, expressed as for example so many millivolts per degree per second. Drift refers to the rate at which the error in a sensor or system accumulates with time. A positioning system based only on IMU/INS data a make unrecognisable the speed profiles over only a couple of minutes, even for the best quality IMU/INSs. Other types of errors are associated with temperature changes on the unit and non-orthogonality when installed. The unit's axes may not be completely aligned with the axes of the vehicle measured when installed. The vibration of the unit also introduces errors into the measurements recorded which requires filtering. Apart from the error filtering, there is a need to correct the measurements from the influence of gravity and centrifugal force.

The IMU unit records the acceleration of the gravitational field. This means that when standing still, the unit records the gravity acceleration in the positive z axis, if the axis are correctly aligned and the unit is perpendicular to the floor. Since the unit is clamped to the vehicle, when it tilts or rolls due to forward movement, and or vibrations, the gravity vector is no longer aligned to the z axes. Hence, the gravity acceleration vector is now decomposed into z and x or y (or both) depending on what the vehicle is experiencing (decomposes in y if vehicle is rolling and x if vehicle is pitching).

The other correction required is the centrifugal force influence on the measurements as the vehicle turns. When the vehicle is turning over a sharp corner the unit experiences an acceleration due to the centrifugal force. This force is the same one experience when riding on a car turning sharply at high speed, which makes the passenger move sideways on curves.

The errors inherent from the correction of this force can be minimised when performing measurements if the IMU/INS is installed on the centre of gravity of the vehicle. This will eliminate the levering effect increased by the centrifugal force where the distance between the IMU/INS and the centre of gravity of the vehicle plays an important part. However, many times it is not possible to install the unit on the centre of gravity and it had to be installed in the most convenient place. Therefore, correction for centrifugal force is required according to the yaw gyro rate measured by the unit. This correction is more important when analysing the measurements for the vehicle carrying the sensor.

Since the IMU/INS is fixed to the carrying vehicle, its axis will remain the same as the vehicle's when it moves along a specific trajectory. However, the IMU/INSs coordinate system will be rotating constantly in the absolute frame of reference. This can be determined from the yaw gyro rate for the 2D case where it only rotates along the z axis. For the 3D more general case Euler angles should be used. These angles allow the transformation of vectors from one coordinate frame to another, and it is based on three successive rotations about different axes. The Euler angles ($\phi$, $\theta$ and $\psi$) are defined as follows:

Rotation through angle $\phi$ about reference x axis
Rotation through angle $\theta$ about reference y axis
Rotation through angle $\psi$ about reference z axis This type of representation is popular because of the physical significance of the Euler angles which correspond to the angles which would be measured by angular pick-offs between a set of three gimbals in a stable platform inertial navigation system. Considering the Euler angle theory, the relationship between the gimbal rates (d$\phi$/dt, d$\theta$/dt and d$\psi$/dt) and the body rates in each of the axes ($\omega$x, $\omega$y, and $\omega$z) is according to the following.

$$\frac{d}{dt}\begin{pmatrix}\phi\\ \theta\\ \psi\end{pmatrix} = \begin{pmatrix}\omega_x + \tan\theta(\omega_y\sin\theta + \omega_z\cos\phi)\\ \omega_y\cos\phi - \omega_z\sin\phi\\ \sec\theta(\omega_y\sin\phi + \omega_z\cos\phi)\end{pmatrix}$$

However, the IMU device used in this invention recorded only the yaw rotation rate about the z axis; hence complete attitude integration was not possible. A complete calculation of the Inertial Navigation System taking into account all the errors and corrections following algorithm can be undertaken which takes into account all the errors and corrections explained above. However, this algorithm is for 3-D purposes and can be simplified if it is not necessary to obtain the change in height. For this algorithm to be completely applicable in the present invention study the IMU/INS needs only to record the x and y (pitch and roll) gyro rates.

Even though it is possible to obtain speed profiles from the GPS and the IMU independently, the results are much more accurate and precise when integrating both sets of equipment into one. The preferred aspect of the present invention is to combine the advantage of the short-term precision of IMU/INS and the long-term stability of GPS. The combination provides very accurate positioning of the point where the data is collected. The use of tightly coupled GPS-IMU/INS e.g. by Kalman filtering is particularly preferred.

Data from the IMU/INS and the GPS can be matched by taking note of the time delay between one stream of data recorded and the other.

Figure 8:
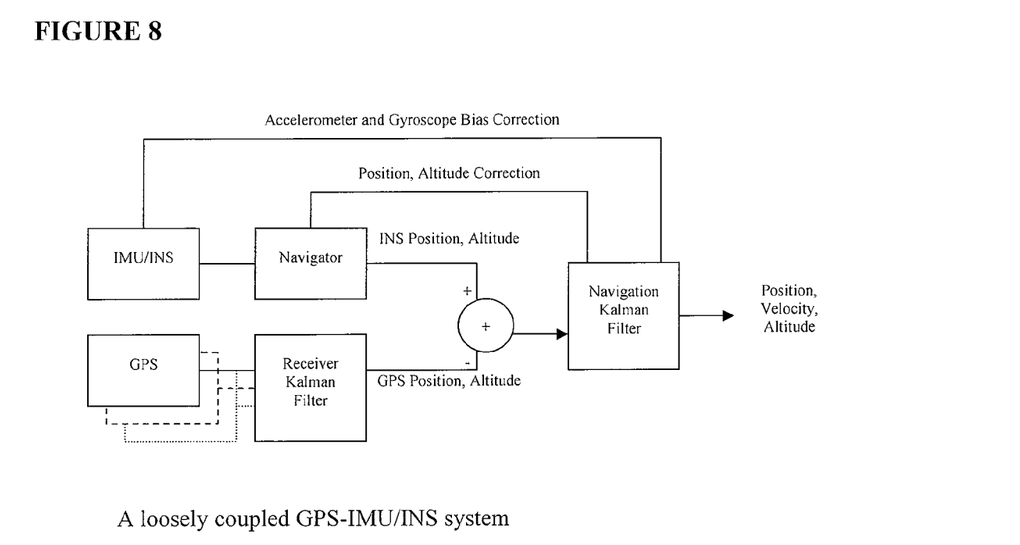
FIG. 8 shows loosely-coupled GPS-IMU/INS system

A common approach to GPS-IMU/INS integration with Kalman filters is termed 'loosely coupled'. With this method a GPS filter (typically EKF or Least-squares recursion) processes the GPS signals and outputs three dimensional position (and possibly velocity) in the standard GPS Earth Centred Earth Fixed (ECEF) reference frame. FIG. 8 shows loosely-coupled GPS-IMU/INS The equations of inertial navigation are essentially integrators meaning inherent noise and biases in the system lead to unbounded, exponential error growth in time. Loosely coupled configurations typically use a second Kalman Filter to predict inertial sensor errors from the equations of inertial navigation. The filter is updated with direct measurement of the position error formed from both the outputs of the IMU/INS and the GPS filter.

Figure 9:
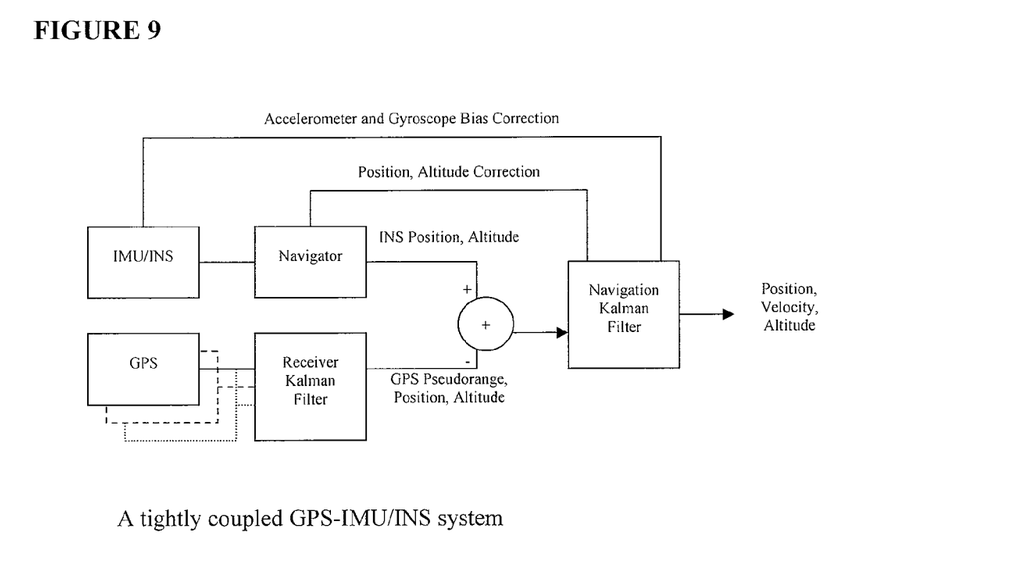
FIG. 9 shows a tightly-coupled GPS-IMU/INS system.

FIG. 9 shows a tightly coupled GPS-IMU/INS System. In tightly coupled integration all position error states and error parameters corresponding to both systems GPS and IMU/

INS are estimated simultaneously within one Kalman filter where double difference GPS carrier phase observations and the IMU/INS accelerometer and gyroscope data are integrated; moreover the IMU/INS errors are fed back directly to the INS sensor.

Figure 10:
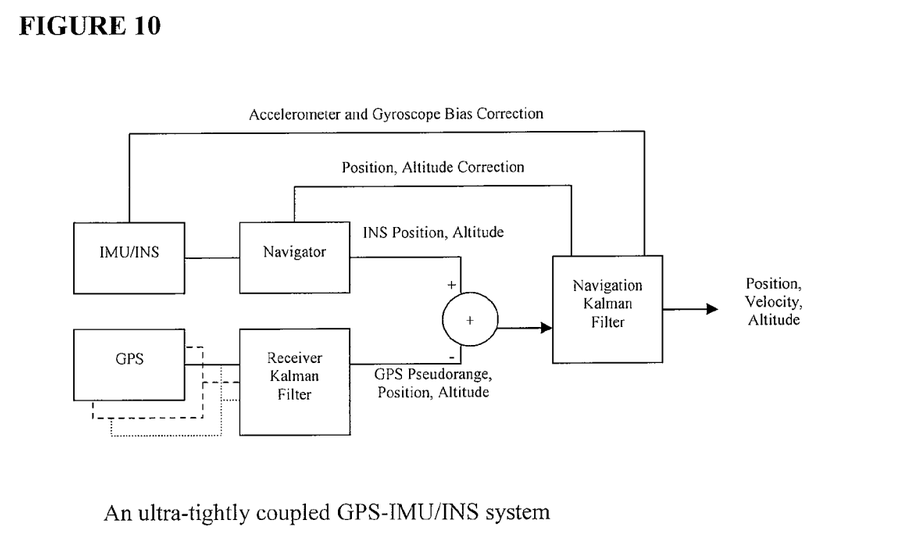
FIG. 10 shows an ultra-tightly coupled GPS-IMU/INS system.

FIG. 10 shows an ultra-tightly coupled GPS-IMU/INS System

The more satellites used in the ranging process the more information the filter has to constrain the inertial navigation solution. In a situation of degraded GPS availability however a tightly coupled configuration is capable of updating the filter with only one visible satellite.

In the gas of a UV-spectroscopic analyser in the subject of this invention, it serves benefit to the sensitivity of the device if one of its dimensions is sufficiently large i.e. that the unit is long. Unlike more traditional internal compact positioning devices on vehicles (e.g. SatNav systems), it is desirable to use more than one GPS receiver such that additional information such as vehicle direction can be inferred. Additionally, multiple GPS receivers can be used to improve height measurement.

This mobile apparatus comprises an IMU/INS (consisting of a plurality of gyroscopes and accelerometers) which is coupled via an RS232 or USB connection to data processing equipment, which may be separate or embedded within the mobile apparatus. One or more GPS receivers are also connected to the processing unit. Where multiple GPS receivers are used, it is preferred they are located at the extremities of the device or vehicle.

This apparatus can be placed on the roof of a vehicle to detect gases in the atmosphere. The gas sampling rate is dependent on the spatial resolution required. For instance, if a one meter resolution is required and the vehicle is travelling at five meters a second, then five samples per second would be required. If the vehicle is stationary at traffic lights for a long period of time, then a longer period of sampling may be required. Additionally spectroscopic sampling times for data aggregation is varied for correlated from a series of continuous measurements such that noise is reduced without degrading the spatial resolution. Such an approach may be specific to each gas being measured.

A full "six degree of freedom" Inertial Measurement Unit (IMU)/Inertial Navigation System (INS) can provide 3D acceleration, speed and trajectory information. A typical IMU/INS consists of three accelerometers and three gyroscopes mounted in a set of three orthogonal axes. The IMU/INS measures the acceleration and the rotation rate of the vehicle in all three dimensions.

The IMU sampling rate should preferably be as high as possible to capture vehicle linear/rotational acceleration events. However, through the time-based double integration of these samples, errors will accumulate, which is where the coupling of GPS assists to effectively draw-down the integration error. In the meantime, the IMU/INS provides information at a higher time-resolution as to the vehicle/person movements. Accurate information on the position of the sensor in all conditions is crucially important, such as in built-up areas, tunnels, cases where a limited number of satellites are available or that the vehicle/movement is not predictable.

The Kalman filter is the preferred way of coupling states from the IMU/INS and GPS data measurements simultaneous. The premise of a Kalman filter is to model both the physical effects and measurement errors at the same time. Consider the nonlinear discrete-time system:

$$x(k+1)=f[x(k),k]+G(k+1,k)w(k)$$

$$z(k+1)=h[x(k+1)k+1]+v(k+1)$$

where x(k) is the state of the system at k, and z(k) is the measurement vector. The vectors w(k) and v(k) are the system noise and measurement noise respectively.

The EKF applies the Kalman filter to nonlinear systems by simply linearising all the nonlinear models so that the traditional linear Kalman filter equations can be applied. The extended Kalman filter (EKF) gives the estimate and the covariance $$\hat{x}(k+1|k+1)=\hat{x}(k+1|k)+K(k+1)[z(k+1)-\hat{z}(k+1|k)]$$

$$P(k+1|k+1)=[I-K(k+1)H(k+1)]P(k+1|k)$$

The prediction of the states and its covariance are $$\hat{x}(k+1|k)=f[\hat{x}(k|k),k]$$

$$P(k+1|k)=F(k+1,k)P(k|k)F^T(k+1,k)+G(k+1,k)Q(k)G^T(k+1,k)$$

The prediction of measurements is $$\hat{z}(k+1|k)=h[\hat{x}(k+1|k),k+1]$$

The Kalman gain matrix is $$K(k+1)=P(k+1|k)H^T(k+1)[H(k+1)P(k+1|k)H^T(k+1)+R(k+1)]^{-1}$$

where F(k+1,k) and H(k+1) are the Jacobian matrices associated with f and h, respectively $$F(k+1,k) = \frac{\partial}{\partial x} f[\hat{x}(k|k), k]$$

$$H(k+1,) = \frac{\partial}{\partial x} h[\hat{x}(k+1|k), k+1]$$

Figure 5:
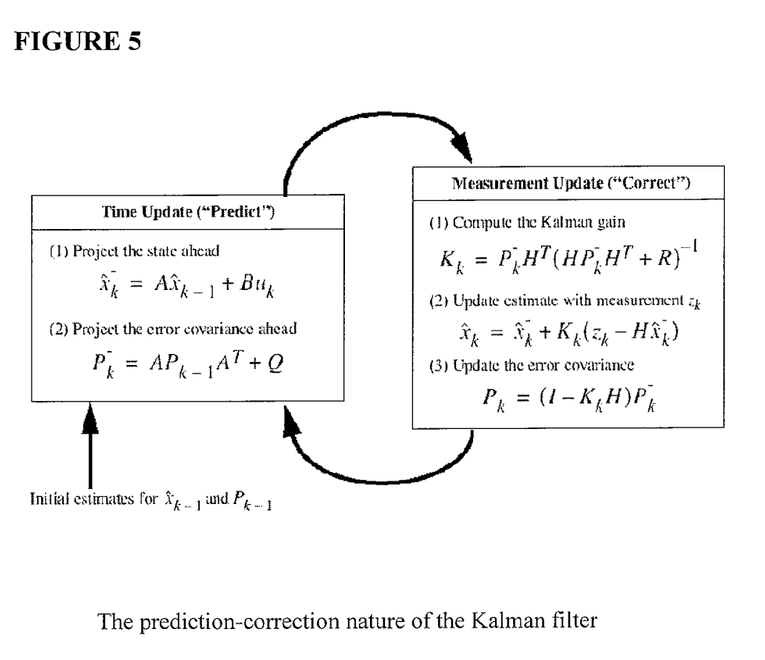
FIG. 5 illustrates the prediction-correction nature of the Kalman filter
Figure 6:
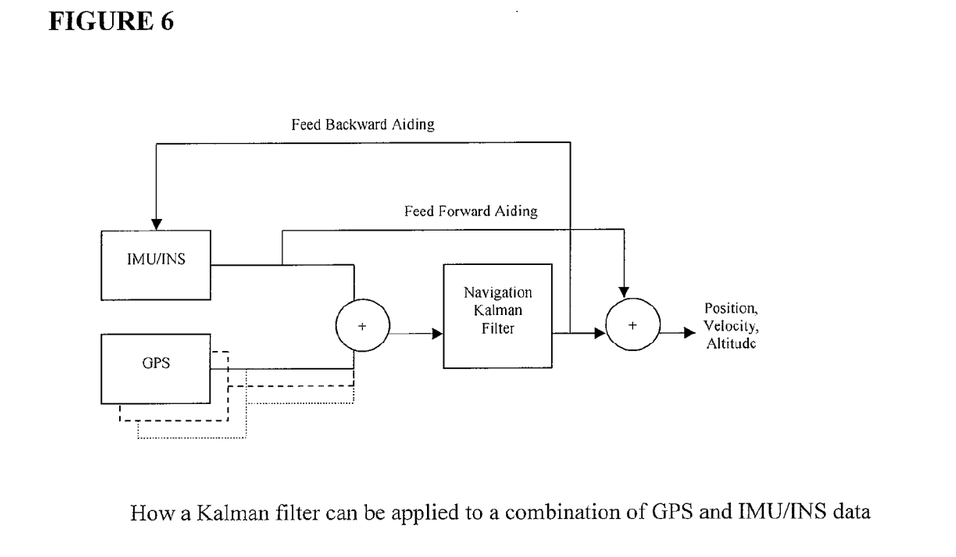
FIG. 6 shows how a Kalman filter can be applied to a combination of GPS and IMU/INS data

A summary of the Kalman algorithm is shown in FIG. 5.

Sampled data can be collected from multiple units and communicated by wireless means (such as WiFi, or Bluetooth) back to a centralised server (or processed by the units themselves via grid computing) where the data is constructed into a time-variant pollution map. The networking can either be infrastructure or 'ad hoc' via the units themselves. It is also intended that the data form the basis of input into a predictive dispersion model for integration with operation research based tools.

Information from the gas sensor can be processed prior to or post transmission to the central server. The sensors can be adapted to measure additional information other than gas concentration, such as temperature and humidity.

The entire volume of data collected from the measuring apparatus, namely the sensor information and the coupled positional information, is imported as data packets into a server and can be warehoused on the same server. Data points representing gas concentration peaks can be extracted and formed into new, reduced data sets for further analysis. The reduced data sets can be converted into database files and then imported into a GIS software system. Using the GIS software, the data can be displayed and manipulated to perform a variety of analyses. The data sets can be combined with the GPS-IMU/INS data to provide a map of pollution. A unique colour, symbol, or extruded height rendered in 3-D, can be assigned to each pollutant and to the concentration of that pollutant corresponding to a ppb-v value in order to analyse spatial changes in pollutant concentration measurements over time. Each data point is tagged with information regarding date, time, and accurate location, as well as statistical summaries or time-based trend plots. Any major changes in pollutant level can be analysed using the tagged information. The information can be used in conjunction with observation notes made by operatives driving the vehicles on which the analysers are located.

Spatially plotted data can be superimposed onto a high resolution (say 1 meter) IKONOS satellite image to view data point location in relation to surface features such as roads, buildings, rivers, and so on. Pollutant emission sources can easily be identified, and real time mapping allows the changes over time of the pollutant sources to be analysed, for example cars at busy road junctions, vessels in harbours, and so on. Other factors such as atmospheric conditions can also be built into the mapping system to analyse wind effects, heat and so on.

The continuity of the data map may be provided by interpolation against measurements from the sensor within a determined time period, or time-cyclical assumption. The overall map can also be an output from a data-driven dispersion model, such as fuzzy, computational fluid dynamics, or source-based dispersion models known in the art may be employed in the mapping calculations.

Sampling periods can be determined based on sensor velocity and concentration. The sample period may be varied as required, either by the central server or by the local sensor microprocessor unit. The ability to vary sample period in accordance with SNR and/or spatial resolution trade-offs is seen as a core part of the method.

The measurement of wind-speed and direction (such as from a compact anemometer) as part of the device is required to attribute the source and/or direction of dispersal. Accurate velocity measurement and orientation data from the device's positioning system is critical for the meaningful operation of this system. In addition, the units ability to capture video images on the occurrence of certain events will also be required in some places.

The level of pollution of automotive vehicles is dependent heavily on the number of transients experienced while driving. The accurate prediction of vehicle acceleration by traffic modelling and control systems is augmented well by the provision of acceleration data from the unit.

The spectrometer/gas cell sampling and averaging rate of the unit is adjusted to account for the vehicle speed to allow for a similar spatial resolution as the vehicle reaches higher speeds. The invention entails that the noise reduction on the system take into account vehicle speed, position, direction as well as concentration variations so as to optimise the signal-to-noise ratio (SNR). Since any filtering, such as Kalman filtering on the concentration levels over time needs to take into account vehicle speed, such data needs to be coupled through inclusion as a state variable within the concentration Kalman filter. An example of this is as follows: The device collects the data into a series of rolling averages, representing differing time-lengths (e.g. 1 second, 10 seconds, 30 seconds). If the vehicle is stationary, it is desirable to weight the concentration to be determined from the rolling average of highest length such that SNR is maximised. If the vehicle is moving quickly then priority is placed on a shorter rolling average such that spatial resolution is preserved with a suitable SNR.

In addition hardware adjustments, such as the source intensity and gas throughput can be increased during higher speeds provided by the GPS-IMU.

Once the data is collected, it is anticipated that Bayesian methods (or similar stochastic techniques) be used to analyse for anomalies in collected datasets over prolonged periods.

The system of the present invention is preferably used in ground based vehicles, as shown in FIG. 3. However, the apparatus can also be carried in the air, for example in unmanned aerial vehicles (UAV's). This can provide a 3-D and real time map of pollution levels, or measure pollution at a fixed height. Coupled GPS/IMU is particularly important if UAV's are to be used, to allow for pitch and yaw. If a UAV is used, then information from an altimeter is fed into the navigation system to provide information on the height of the vehicle. The altitude information is then also included in the packet information sent back by the processor to the server. Thus a measurement can be made of, e.g. pollution at a fixed height above ground level. The use of sensors on UAV's is well known, but the present invention can utilise this information to provide a real time map of the measured environmental factor.

Although the present invention has been particularly described in relation to the mapping of pollutant levels, it will be appreciated that the mapping can be used in relation to any other measurable data, such as particulate levels, toxic gas levels, radiation levels, light levels and noise levels.

The invention claimed is:

1. A system for mapping environmental factors in the atmosphere, comprising:
    a mobile detection apparatus, comprising:
        a sensor for detecting environmental factors in a plurality of atmospheric samples taken at an adjustable sample rate and providing atmospheric sample data;
        a navigation system for tracking a geographic position of the sensor, the navigation system comprising: a first navigation unit comprising a Global Positioning System ("GPS") receiver, and a second navigation unit comprising an Inertial Navigation System ("INS") comprising one or more Inertial Measurement Units ("IMU");
        a processing unit coupled to the sensor and the navigation system and configured to:
            integrate the first navigation unit and the second navigation unit to calculate position data and velocity data,
            adjust the adjustable sampling rate based on the velocity data such that a sample period of the sensor is shorter when a velocity is higher and longer when the velocity is lower,
            receive, from the sensor, the data related to the plurality of atmospheric samples taken at the adjustable sampling rate, and
            combining the atmospheric sample data with position data into data packets; and
    a server including a database where the data packets from the mobile detection apparatus are stored and processed.

2. The system according to claim 1, wherein the sensor is selected from a group consisting of an ultraviolet spectrometer, an ultraviolet-light spectrometer, an infrared spectrometer, or a combination thereof.

3. The system according to claim 2, wherein the sensor detects within a wavelength range of 160-500 nm.

4. The system according to claim 1, further comprising a wind velocity unit to collect wind velocity data, the processor utilizing the wind velocity data in conjunction with the geographical location data to predict a distribution of environmental factors.

5. The system of claim 1, wherein integrating the first navigation unit and the second navigation unit comprises calculating continuously refined position data.

6. The system of claim 1, the server processing the data packets to generate a map of environmental factors in relation to known points.

7. The system of claim 1, the server processing additional data from a second mobile detection apparatus.

8. A device for use in mapping environmental factors in the atmosphere, comprising:
- a sensor for detecting environmental factors in a plurality of atmospheric samples taken at an adjustable sample rate and providing atmospheric sample data;
- a navigation system for tracking a geographic position of the sensor the navigation system comprising: a first navigation unit comprising a Global Positioning System ("GPS") receiver, and a second navigation unit comprising an Inertial Navigation System ("INS") comprising one or more Inertial Measurement Units ("IMU");
- a processing unit coupled to the sensor and the navigation system and configured to:
  - integrate the first navigation unit and the second navigation unit to calculate position data and velocity data,
  - adjust the adjustable sampling rate based on the velocity data such that a sample period of the sensor is shorter when a velocity is higher and longer when the velocity is lower,
  - receive, from the sensor, the data related to the plurality of atmospheric samples taken at the adjustable sampling rate,
  - combine the atmospheric sample data with position data into data packets, and
  - transmit, the data packets to a server.

9. The device according to claim 8, wherein the sensor is selected from a group consisting of an ultraviolet spectrometer, an ultraviolet-light spectrometer, an infrared spectrometer, or a combination thereof.

10. The device according to claim 9, wherein the sensor detects a wavelength range of 160-500 nm.

11. The device according to claim 8, further comprising a wind velocity unit to collect wind velocity data, the processor utilizing the wind velocity data in conjunction with the geographical location data to predict a distribution of environmental factors.

12. The device of claim 8, wherein integrating the said first navigation unit and the second navigation unit comprises calculating continuously refined position data.

13. A method of mapping environmental factors in the atmosphere, comprising:
- detecting, with a sensor of a mobile detection apparatus, environmental factors in a plurality of atmospheric samples taken at an adjustable sample rate;
- tracking, by a navigation system of the mobile detection apparatus, a geographical position of the sensor, the navigation system comprising: a first navigation unit comprising a Global Positioning System ("GPS") receiver, and a second navigation unit comprising an Inertial Navigation System ("INS") comprising one or more Inertial Measurement Units ("IMU");
- integrating, by a processor of the mobile detection apparatus, the first navigation unit and the second navigation unit to calculate position data and velocity data;
- adjusting, by the processor, the adjustable sampling rate based on the velocity data such that a sample period of the sensor is shorter when a velocity is higher and longer when the velocity is lower;
- receiving, from the sensor, the data related to the plurality of atmospheric samples taken at the adjustable sampling rate;
- combining, by the processor, the atmospheric sample data with position data into data packets; and
- transmitting, by the processor, the data packets to a server.

14. The method according to claim 13, the processor transmitting the data packets to the server for storage, visualization, and analysis.

15. The method of claim 13, wherein integrating the first navigation unit and the second navigation unit comprises calculating continuously refined position data.

16. The method of claim 13, further comprising:
- collecting, using a wind velocity unit of the mobile detection apparatus, wind velocity data; and
- predicting, by the processor, a distribution of environmental factors using the wind velocity.

17. The method of claim 16, the method further comprising generating, by the server based on the data packets, a map of environmental factors in relation to known points.

* * * * *